(12) United States Patent
Cheng et al.

(10) Patent No.: US 11,471,034 B2
(45) Date of Patent: Oct. 18, 2022

(54) METHOD AND DEVICE FOR DISTINGUISHING PLAQUE AND CALCULUS

(71) Applicant: Quanta Computer Inc., Taoyuan (TW)

(72) Inventors: Kai-Ju Cheng, Taoyuan (TW);
Hsin-Lun Hsieh, Taoyuan (TW);
Chin-Yuan Ting, Taoyuan (TW);
Tsung-Hsin Lu, Taoyuan (TW);
Huan-Tang Wu, Taoyuan (TW);
Shao-Ang Chen, Taoyuan (TW);
Yu-Hsun Chen, Taoyuan (TW);
Jia-Chyi Wang, Taoyuan (TW);
Chih-Wei Sung, Taoyuan (TW);
Huan-Pin Shen, Taoyuan (TW)

(73) Assignee: QUANTA COMPUTER INC., Taoyuan (TW)

( * ) Notice: Subject to any disclaimer, the term of this patent is extended or adjusted under 35 U.S.C. 154(b) by 355 days.

(21) Appl. No.: 16/774,279

(22) Filed: Jan. 28, 2020

(65) Prior Publication Data
US 2021/0059511 A1    Mar. 4, 2021

(30) Foreign Application Priority Data

Aug. 30, 2019   (TW) ................................ 108131156

(51) Int. Cl.
*G06K 9/00* (2022.01)
*A61B 1/04* (2006.01)
(Continued)

(52) U.S. Cl.
CPC .............. *A61B 1/043* (2013.01); *A61B 1/063* (2013.01); *A61B 1/24* (2013.01); *G06T 7/0012* (2013.01);
(Continued)

(58) Field of Classification Search
CPC ........... A61B 1/043; A61B 1/063; A61B 1/24; A61B 1/00016; A61B 5/0088;
(Continued)

(56) References Cited

U.S. PATENT DOCUMENTS

| | | |
|---|---|---|
| 9,247,882 B2 | 2/2016 | Hakomori et al. |
| 2013/0034826 A1 | 2/2013 | Walsh et al. |

(Continued)

FOREIGN PATENT DOCUMENTS

CN    103445761 A    12/2013

OTHER PUBLICATIONS

Chinese language office action dated Jan. 21, 2020, issued in application No. TW 108131156.
(Continued)

*Primary Examiner* — Tom Y Lu
(74) *Attorney, Agent, or Firm* — McClure, Qualey & Rodack, LLP (57) ABSTRACT

A method for distinguishing plaque and calculus is provided. The method is used in a device and includes the following steps: emitting, by a blue light-emitting diode, blue light to illuminate teeth in an oral cavity, wherein the blue light is used to generate autofluorescence of plaque and calculus on the teeth; sensing, by an image sensor, the autofluorescence of plaque and calculus; and distinguishing, by a processor, a plaque area and a calculus area on the teeth based on the autofluorescence.

6 Claims, 6 Drawing Sheets

(51) Int. Cl.
  *A61B 1/06* (2006.01)
  *A61B 1/24* (2006.01)
  *G06T 7/00* (2017.01)
  *A61B 1/00* (2006.01)

(52) U.S. Cl.
  CPC . *A61B 1/00016* (2013.01); *G06T 2207/10064* (2013.01); *G06T 2207/30036* (2013.01)

(58) Field of Classification Search
  CPC ... A61B 5/4547; A61B 5/0071; G06T 7/0012; G06T 2207/10064; G06T 2207/30036; A61C 19/04
  See application file for complete search history.

(56) References Cited

U.S. PATENT DOCUMENTS

| | | |
|---|---|---|
| 2013/0323674 A1 | 12/2013 | Hakomori et al. |
| 2013/0323685 A1* | 12/2013 | Ostler ............ A61K 6/79 522/64 |
| 2016/0166137 A1* | 6/2016 | Hakomori ............ A61B 5/0013 433/29 |
| 2017/0303791 A1 | 10/2017 | Vermeulen |
| 2019/0231492 A1 | 8/2019 | Sabina et al. |

OTHER PUBLICATIONS

European Search Report dated Aug. 25, 2020, issued in application No. EP 20165693.1.

* cited by examiner

METHOD AND DEVICE FOR DISTINGUISHING PLAQUE AND CALCULUS

CROSS REFERENCE TO RELATED APPLICATIONS

This application claims priority of Taiwan Patent Application No. 108131156, filed on Aug. 30, 2019, the disclosure of which is incorporated by reference herein in its entirety.

BACKGROUND OF THE INVENTION

Field of the Invention

The present disclosure relates to a method and device for distinguishing plaque and calculus. Specifically, the present disclosure relates to a method and device for distinguishing plaque and calculus by using the autofluorescence of the plaque and the calculus on teeth.

Description of the Related Art

Caries and periodontal disease are thought to be infectious diseases caused by bacteria in dental plaque and calculus. Removal of dental plaque and calculus is very important for the health of teeth and prevention of cavities.

However, in the field of oral care, dental plaque and calculus are not easy to identify with the naked eye. How to enable dental doctors to know where dental plaque and calculus are when performing oral care on patients has become a problem to be solved today. Therefore, there is a need for a method and device for distinguishing plaque and calculus to help detect plaque and calculus.

BRIEF SUMMARY OF THE INVENTION

The following summary is illustrative only and is not intended to be limiting in any way. That is, the following summary is provided to introduce concepts, highlights, benefits and advantages of the novel and non-obvious techniques described herein. Select, not all, implementations are described further in the detailed description below. Thus, the following summary is not intended to identify essential features of the claimed subject matter, nor is it intended for use in determining the scope of the claimed subject matter.

A method and device for distinguishing plaque and calculus are provided.

In a preferred embodiment, a method for distinguishing plaque and calculus is provided in the disclosure. The method is used in a device and includes the following steps: emitting, by a blue light-emitting diode, blue light to illuminate teeth in an oral cavity, wherein the blue light is used to generate autofluorescence of plaque and calculus on the teeth; sensing, by an image sensor, the autofluorescence of plaque and calculus; and distinguishing, by a processor, a plaque area and a calculus area on the teeth based on the autofluorescence.

In some embodiments, the blue light-emitting diode emits blue light within the same wavelength bands during a time period, and the blue light-emitting diode emits blue light during the time period with a light source output power having a modulation waveform.

In some embodiments, the step of distinguishing a plaque area and a calculus area on the teeth based on the autofluorescence further comprises: distinguishing, by the processor, the plaque area and the calculus area according to a first autofluorescence cycle of the calculus and a second autofluorescence cycle of the plaque during the time period.

In some embodiments, the modulation waveform is a triangular waveform.

In some embodiments, the blue light-emitting diode emits blue light within a wavelength band from 370 nanometers (nm) to 430 nm.

In a preferred embodiment, a device for distinguishing plaque and calculus, comprising: a blue light-emitting diode, emitting blue light to illuminate teeth in an oral cavity, wherein the blue light is used to generate autofluorescence of plaque and calculus on the teeth; an image sensor, sensing the autofluorescence of plaque and calculus; and a processor, distinguishing a plaque area and a calculus area on the teeth based on the autofluorescence.

BRIEF DESCRIPTION OF DRAWINGS

The accompanying drawings are included to provide a further understanding of the disclosure, and are incorporated in and constitute a part of the present disclosure. The drawings illustrate implementations of the disclosure and, together with the description, serve to explain the principles of the disclosure. It should be appreciated that the drawings are not necessarily to scale as some components may be shown out of proportion to the size in actual implementation in order to clearly illustrate the concept of the present disclosure.

DETAILED DESCRIPTION OF THE INVENTION

Various aspects of the disclosure are described more fully hereinafter with reference to the accompanying drawings. This disclosure may, however, be embodied in many different forms and should not be construed as limited to any specific structure or function presented throughout this disclosure. Rather, these aspects are provided so that this disclosure will be thorough and complete, and will fully convey the scope of the disclosure to those skilled in the art. Based on the teachings herein one skilled in the art should appreciate that the scope of the disclosure is intended to cover any aspect of the disclosure disclosed herein, whether implemented independently of or combined with any other aspect of the disclosure. For example, an apparatus may be implemented or a method may be practiced using any number of the aspects set forth herein. In addition, the scope of the disclosure is intended to cover such an apparatus or method which is practiced using other structure, functionality, or structure and functionality in addition to or other than the various aspects of the disclosure set forth herein. It should be understood that any aspect of the disclosure disclosed herein may be embodied by one or more elements of a claim.

The word "exemplary" is used herein to mean "serving as an example, instance, or illustration." Any aspect described herein as "exemplary" is not necessarily to be construed as preferred or advantageous over other aspects. Furthermore, like numerals refer to like elements throughout the several views, and the articles "a" and "the" includes plural references, unless otherwise specified in the description.

It should be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Other words used to describe the relationship between elements should be interpreted in a like fashion (e.g., "between" versus "directly between", "adjacent" versus "directly adjacent", etc.).

Figure 1:
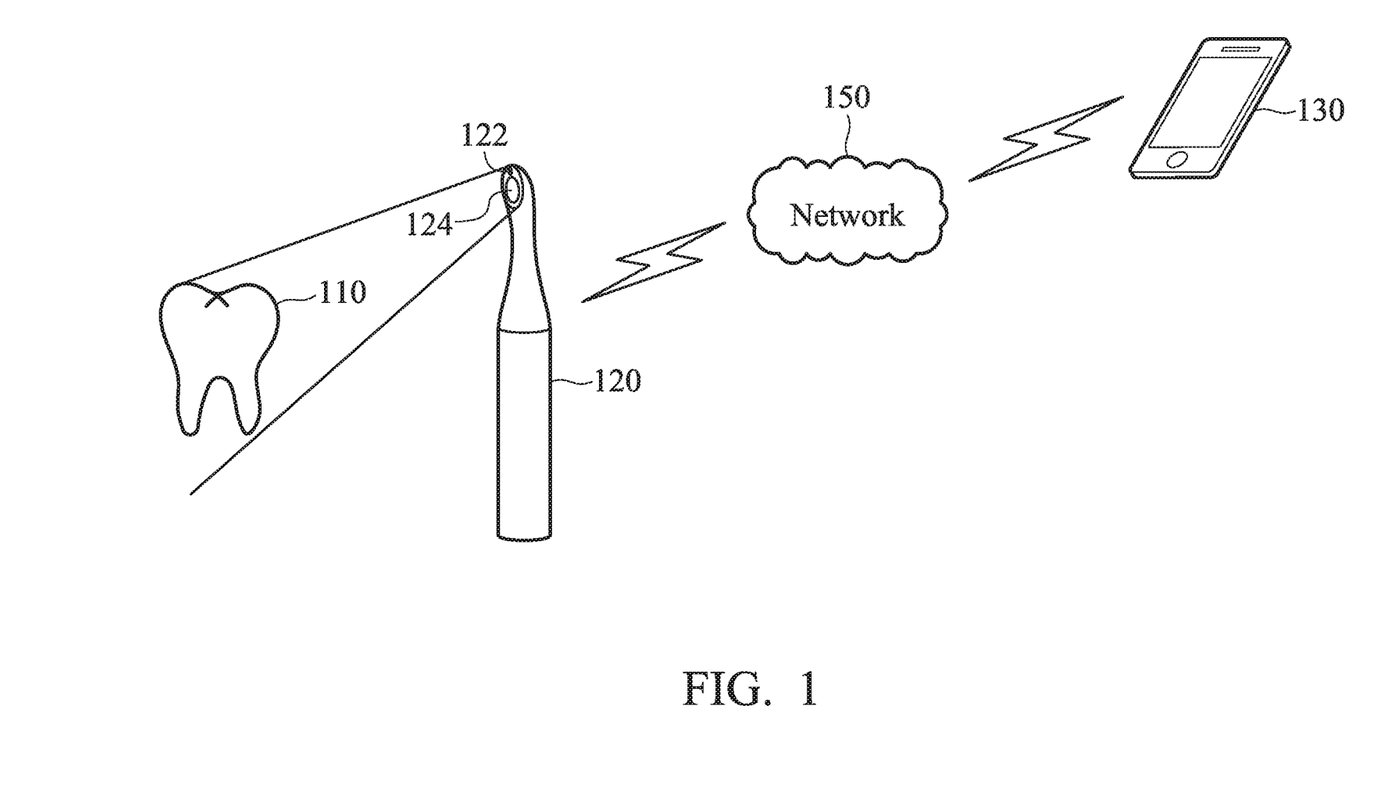
FIG. 1 is a schematic diagram illustrating an operation of examining teeth by an examining device in accordance with an embodiment of the present disclosure.

FIG. 1 is a schematic diagram illustrating an operation of examining teeth 110 by an examining device 120 in accordance with an embodiment of the present disclosure. In FIG. 1, the examining device 120 may at least comprise a blue light-emitting diode 122, an image sensor 124 and a processor (not shown) that can be integrated into the examining device 120.

In some embodiments, the blue light-emitting diode 122 can emit light within a wavelength band in the range from 370 nanometers (nm) to 430 nm to illuminate the teeth 110 in the oral cavity. Specifically, dental plaque and calculus on the teeth 110 generate autofluorescence when the teeth 110 are illuminated with incident blue light within the wavelength bands.

The image sensor 124 is used for sensing the autofluorescence emitted from the plaque and the calculus. In one embodiment, the image sensor 124 may be a single-point photodetector or a photosensitive element which is array type, such as a charge coupled device (CCD) or a complementary metal-oxide semiconductor (CMOS). The single-point photodetector may directly analyze a single pixel, while the photosensitive element which is array type may analyze pixels that belong to the same area of each frame by image processing methods.

The processor, which may be coupled to the image sensor 124, receives autofluorescence results generated from the plaque and calculus sensed by the image sensor 124, and distinguishes those plaque areas and calculus areas located on the teeth 110 based on the autofluorescence.

The examining device 120 can be connected to an electronic device 130 using the network 150 to transmit the images including the plaque area and the calculus area distinguished by the processor to the electronic device 130. Exemplary electronic devices may include a desktop computer, a notebook, a smartphone, a personal digital assistant (PDA), a tablet, or any other device having a display screen. The user may view the dental plaque area and the calculus area on the teeth 110 in the images through the electronic device 130. The network 150 can provide wired and/or wireless networks. The network 150 may also include a local area network (LAN) (e.g., an intranet), a wireless local area network (WLAN) or a Wi-Fi network, a third generation (3G) or a fourth generation (4G) mobile telecommunications network, a wide area network (WAN), the Internet, Bluetooth, or any suitable combination thereof.

In the embodiment, the examining device 120 is integrated with the blue light-emitting diode 122 into a single device. The examining device 120 integrated into the single device may be separated from the blue light-emitting diode 122. It should be noted that the examining device 120 may be a general electronic device such as a dental camera or the like. Although the examining device 120 of FIG. 1 is shown in the form of a dental camera, it should be understood by those skilled in the art that the present disclosure is not limited thereto.

Figure 2:
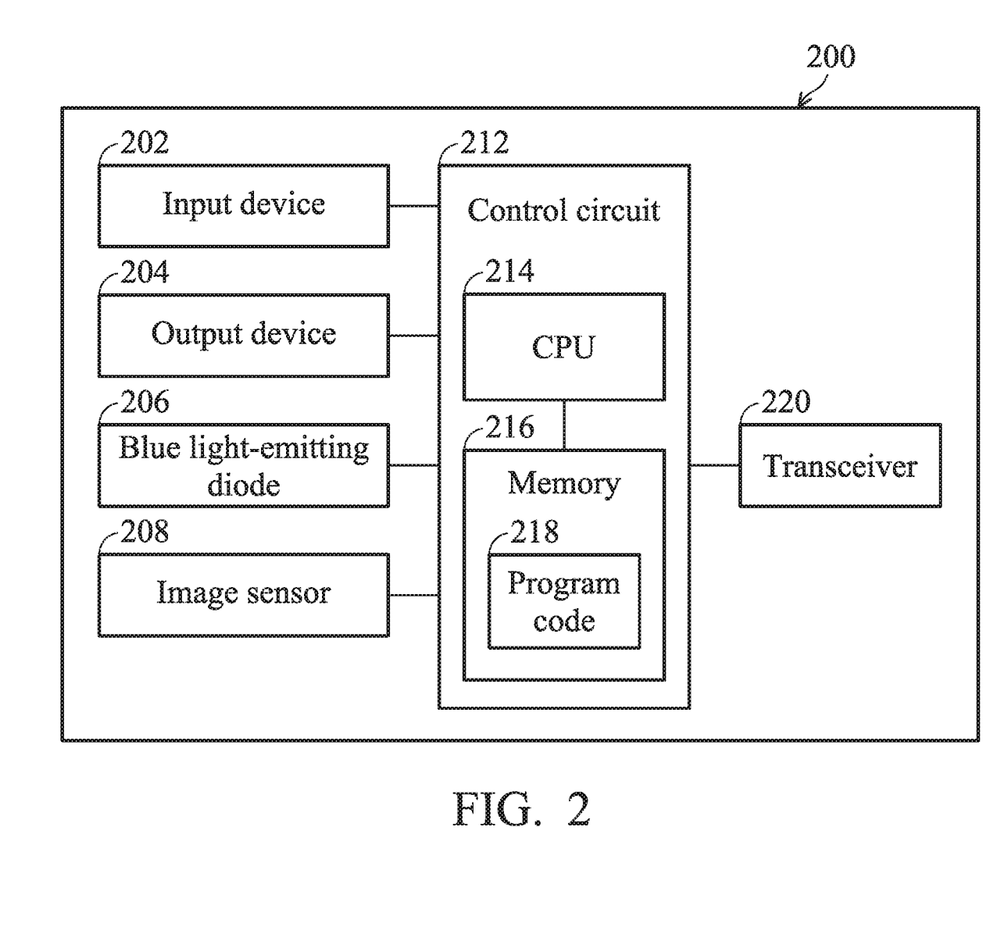
FIG. 2 is a simplified functional block diagram of an examining device according to one embodiment of the present disclosure.

FIG. 2 is a simplified functional block diagram of an examining device 200 according to one embodiment of the present disclosure. As shown in FIG. 2, the examining device 200 can be the examining device 120 of FIG. 1.

In FIG. 2, the examining device 200 may include an input device 202, an output device 204, a blue light-emitting diode 206, an image sensor 208, a control circuit 212 and a transceiver 220. The control circuit 212 can comprise a central processing unit (CPU) 214 and a memory 216.

The examining device 200 can receive signals input by a user through the input device 202, (such as a button) and can output images through the output device 204. The blue light-emitting diode 206 emits blue light within a wavelength band from 370 nanometers (nm) to 430 nm when energized. In another embodiment, the blue light-emitting diode 122 can emit blue light including a wavelength of 405 nm, wherein the blue light including a wavelength of 405 nm may effectively generate detectable autofluorescent emissions between normal teeth tissue and abnormal one.

The image sensor 208 is used for image sensing in the oral cavity and transmits the images of the oral cavity to the CPU 214 to provide the CPU 214 to distinguish the plaque area and calculus area located in the oral cavity based on the autofluorescence in the images.

The memory 216 can store a program code 218. The control circuit 212 executes the program code 218 in the memory 216 through the CPU 214, thereby controlling the operation performed by the examining device 200. The transceiver 220 is used to receive and transmit wireless signals, delivering received signals to the control circuit 212, and outputting signals generated by the control circuit 212 wirelessly.

Figure 3:
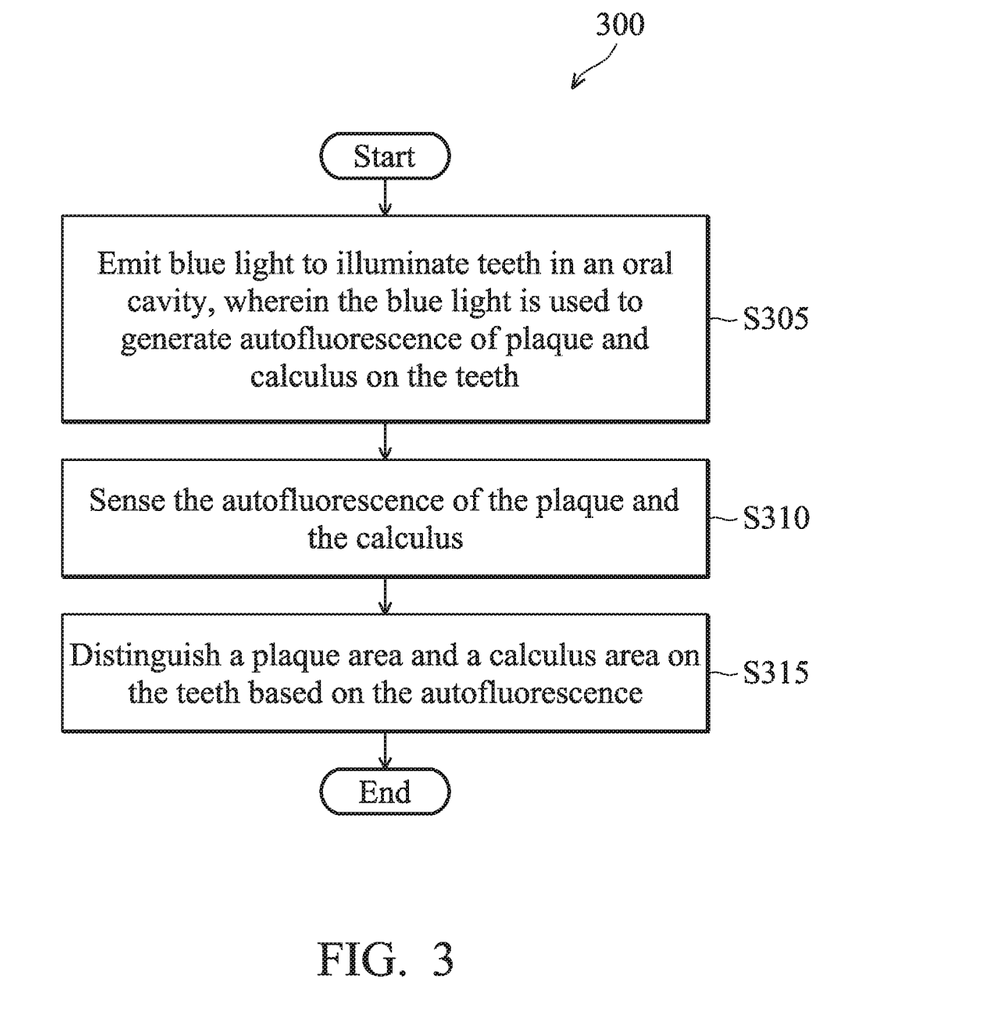
FIG. 3 is a flow diagram illustrating a method for distinguishing plaque and calculus according to an embodiment of the present disclosure.

FIG. 3 is a flow diagram 300 illustrating a method for distinguishing plaque and calculus according to an embodiment of the present disclosure. The method is used in the processor of the examining device 120 of FIG. 1.

In step S305, a blue light-emitting diode of the examining device emits blue light to illuminate teeth in an oral cavity, wherein the blue light is used to generate autofluorescence of plaque and calculus on the teeth. In one embodiment, the blue light-emitting diode emits blue light within a wavelength band from 370 nanometers (nm) to 430 nm. In another embodiment, the blue light-emitting diode emits blue light within the same wavelength bands during a time period, and the blue light-emitting diode emits blue light during the time period with a light source output power having a modulation waveform.

Next, in step S310, an image sensor of the examining device senses the autofluorescence of the plaque and the calculus. In step S315, a processor of the examining device distinguishes a plaque area and a calculus area on the teeth based on the autofluorescence.

The following will describe in detail how the processor distinguishes the plaque area and the calculus area on the teeth based on the autofluorescence of the plaque and the calculus in step S315.

Figure 4:
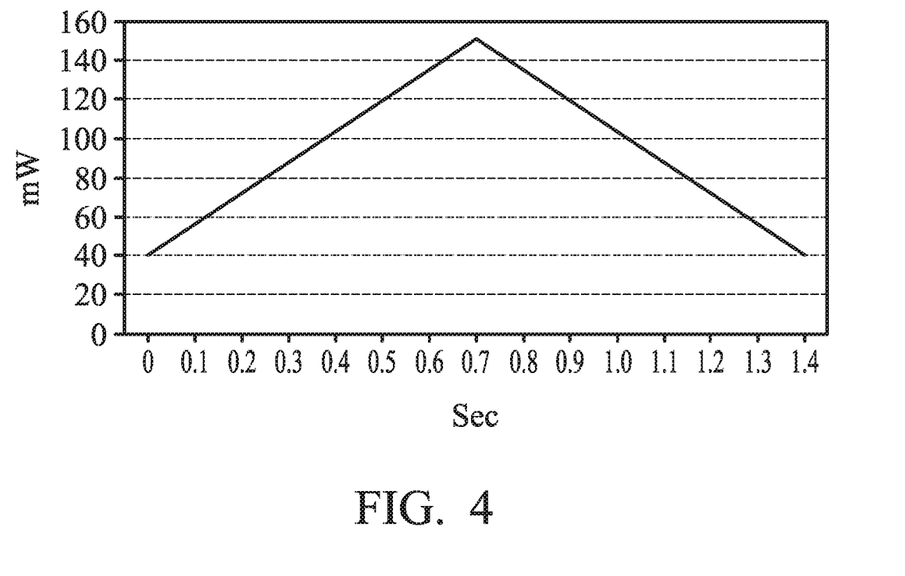
FIG. 4 is a schematic diagram of the wattage modulation of the output power of the blue light-emitting diode according to an embodiment of the disclosure.

In the embodiment, it is assumed that the blue light-emitting diode emits blue light including a wavelength of 395 nm. The processor may adjust the output power of the blue light-emitting diode to determine the luminous intensity of the blue light emitted by the blue light-emitting diode. FIG. 4 is a schematic diagram of the wattage modulation of the output power of the blue light-emitting diode according to an embodiment of the disclosure. As shown in FIG. 4, the processor controls the blue light-emitting diode to increase/decrease the wattage of the output power of the blue light-emitting diode at a fixed modulation interval during a time period. In one embodiment, the lower bound of the length of modulation time interval must be greater than the exposure time of the image sensor, while the upper bound is not particularly limited and can be adjusted according to the needs and the actual output effects, and therefore it should not be limited in the disclosure. In another embodiment, the modulation time interval is approximately an integer multiple of the exposure time of the image sensor to achieve better results.

In the embodiment, the output power of the blue light-emitting diode starts from 41.8 milliwatts (mW). The processor increases the output power by about 15.5 mW at a fixed modulation interval until 151.1 mW. Then, the processor reduces the output power by about 15.5 mW at a fixed modulation interval until 41.8 mW. The output power of the blue light-emitting diode can cyclically output in this way in the next time period. In addition, a modulation time interval of 100 milliseconds (ms) and an exposure time of the image sensor of 33 milliseconds are used in FIG. 4. Therefore, during a time period (for example, 1.4 seconds), the output power of the light source is presented in a triangular waveform.

In some embodiments, the output power of the light source may be presented in a trapezoidal waveform, a sawtooth waveform, or a sine waveform. Therefore, the present disclosure should not be limited to the embodiment shown in FIG. 4.

Figure 5:
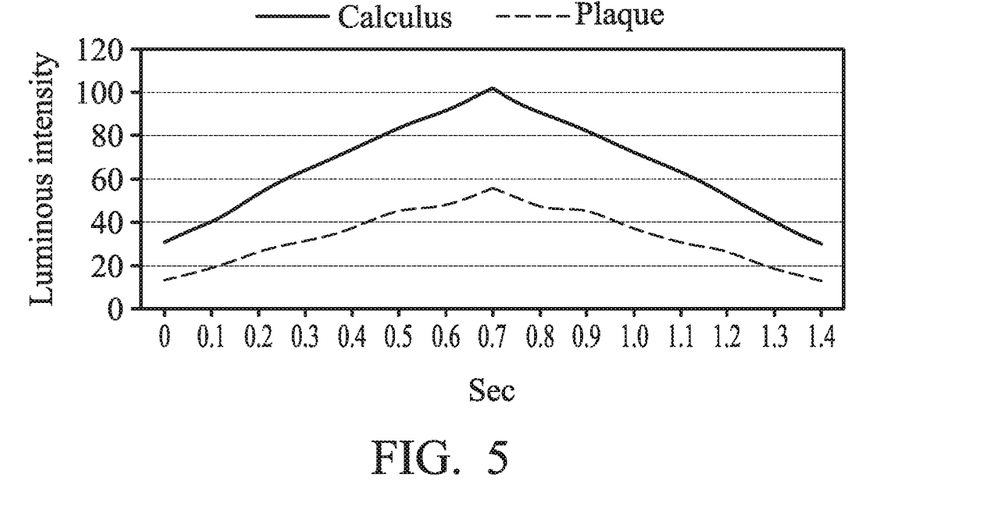
FIG. 5 is a schematic diagram of the intensities of autofluorescence of plaque and calculus according to an embodiment of the disclosure.

Next, the processor may analyze the intensity of autofluorescence of the plaque and the calculus sensed by the image sensor. Since the concentration of bacteria that emit red autofluorescence (for example, Gram-negative bacteria) increases as plaque progresses to calculus, the intensity changes of the autofluorescence of the plaque and the calculus are shown in FIG. 5.

Figure 6:
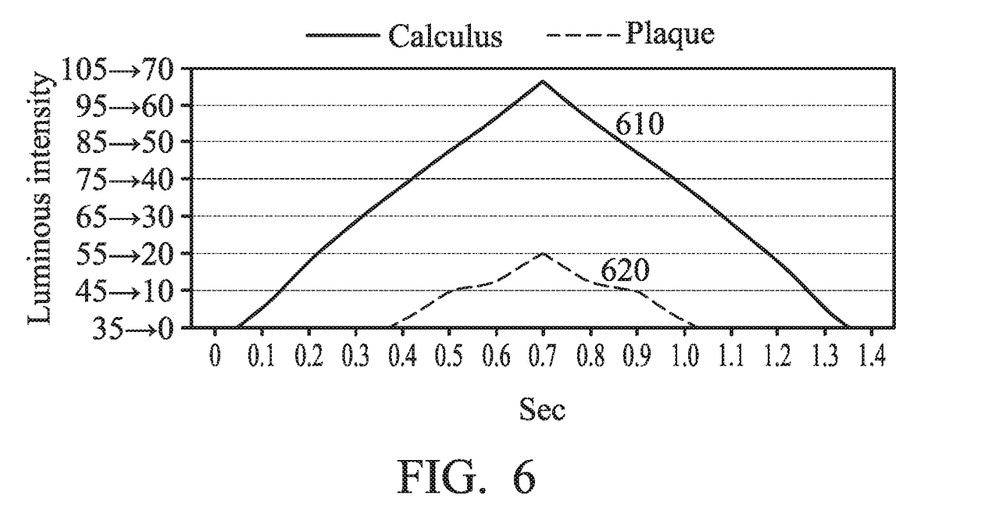
FIG. 6 is a schematic diagram of the intensities of autofluorescence of plaque and calculus according to an embodiment of the disclosure.

Specifically, the processor may set the luminous intensity 35 to zero to obtain FIG. 6. It should be noted that although the luminous intensity 35 is set to zero in FIG. 6 as an example, in some embodiments, the processor may select any value from the luminous intensity between 25 and 45 as the zero point, and the disclosure should not be limited to what is shown in FIG. 6. As shown in FIG. 6, it is easy to observe that the plaque and calculus have significantly different luminous cycle changes. The processor can distinguish the plaque area from the calculus area according to the first autofluorescence cycle 610 of the calculus and the second autofluorescence cycle 620 of the plaque during the time period.

Figure 7A:
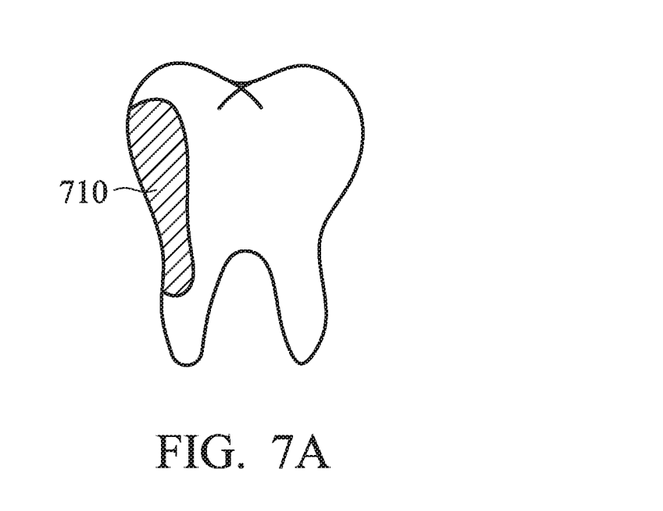
FIGS. 7A and 7B are schematic diagrams of the plaque and calculus areas according to an embodiment of the disclosure.
Figure 7B:
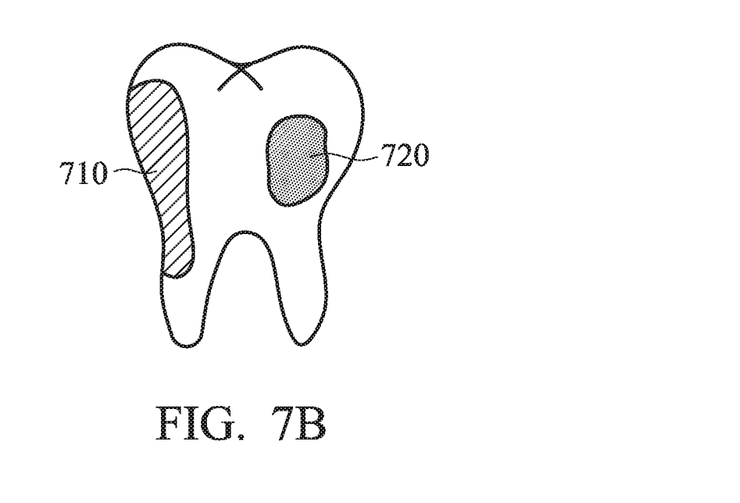

For example, within 0 to 0.35 seconds, since the autofluorescence of calculus can be detected first, the processor may determine the calculus area during the time period of 0 to 0.35 seconds. As shown in FIG. 7A, the processor determines the part as the calculus area 710 according to the location of autofluorescence within 0 to 0.35 seconds. From the time of 0.35 seconds (that is, when the luminous intensity of blue light is higher than a threshold value), the autofluorescence of plaque begins to be detected. As shown in FIG. 7B, the processor determines the part as the plaque area 720 according to the location of autofluorescence on the teeth within 0.35 to 1.05 seconds.

It should be noted that although the wavelength of the blue light-emitting diode is 395 nanometers (nm) as an example in FIG. 4, it should not be limited in the disclosure. Similarly, the intensities of autofluorescence of plaque and calculus in FIG. 5 and FIG. 6 may vary depending on the configurations of different components (such as the blue light-emitting diode and the image sensor), and therefore the present disclosure should not be limited to what is shown in FIG. 5 and FIG. 6.

As shown above, the method and device for distinguishing plaque and calculus in the present disclosure distinguish the plaque area from the calculus area based on the autofluorescence cycles of the plaque and the calculus to achieve the purpose of detecting the plaque area and/or the calculus area.

In addition, in the above exemplary device, although the method has been described on the basis of the flow diagram using a series of steps or blocks, the present disclosure is not limited to the sequence of the steps, and some of the steps may be performed in a different order than that of the remaining steps or may be performed simultaneously with the remaining steps.

In addition, the CPU 214 could execute the program code 218 to perform all of the above-described actions and steps or others described herein.

Various aspects of the disclosure have been described above. It should be apparent that the teachings herein may be embodied in a wide variety of forms and that any specific structure, function, or both being disclosed herein is merely representative. Based on the teachings herein one skilled in the art should appreciate that an aspect disclosed herein may be implemented independently of any other aspects and that two or more of these aspects may be combined in various ways. For example, an apparatus may be implemented or a method may be practiced using any number of the aspects set forth herein. In addition, such an apparatus may be implemented or such a method may be practiced using another structure, functionality, or structure and functionality in addition to or other than one or more of the aspects set forth herein.

Those with skill in the art will understand that information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

Those skilled in the art will further appreciate that the various illustrative logical blocks, modules, processors, means, circuits, and algorithm steps described in connection with the aspects disclosed herein may be implemented as electronic hardware (e.g., a digital implementation, an analog implementation, or a combination of the two, which may be designed using source coding or some other technique), various forms of program or design code incorporating instructions (which may be referred to herein, for convenience, as "software" or a "software module"), or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in ways that vary for each particular application, but such implementation decisions should not be interpreted as causing a departure from the scope of the present disclosure.

In addition, the various illustrative logical blocks, modules, and circuits described in connection with the aspects disclosed herein may be implemented within or performed by an integrated circuit ("IC"), an access terminal, or an access point. The IC may comprise a general purpose processor, a digital signal processor (DSP), an application specific integrated circuit (ASIC), a field programmable gate array (FPGA) or another programmable logic device, discrete gate or transistor logic, discrete hardware components, electrical components, optical components, mechanical components, or any combination thereof designed to perform the functions described herein, and may execute codes or instructions that reside within the IC, outside of the IC, or both. A general-purpose processor may be a microprocessor, but in the alternative, the processor may be any processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

It should be understood that any specific order or hierarchy of steps in any disclosed process is an example of a sample approach. It should be understood that the specific order or hierarchy of steps in the processes may be rearranged while remaining within the scope of the present disclosure. The accompanying method claims present elements of the various steps in a sample order, and are not meant to be limited to the specific order or hierarchy presented.

While the disclosure has been described by way of example and in terms of exemplary embodiment, it is to be understood that the disclosure is not limited thereto. Those who are skilled in this technology can still make various alterations and modifications without departing from the scope and spirit of this disclosure. Therefore, the scope of the present disclosure shall be defined and protected by the following claims and their equivalents.

What is claimed is:

1. A method for distinguishing plaque and calculus, used in a device, comprising:
    emitting, by a blue light-emitting diode, blue light to illuminate teeth in an oral cavity, wherein the blue light is used to generate autofluorescence of plaque and calculus on the teeth;
    sensing, by an image sensor, the autofluorescence of plaque and calculus; and
    distinguishing, by a processor, a plaque area and a calculus area on the teeth based on the autofluorescence;
    wherein the blue light-emitting diode emits blue light within the same wavelength bands during a time period, and the blue light-emitting diode emits blue light during the time period with a light source output power having a modulation waveform;
    wherein the step of distinguishing a plaque area and a calculus area on the teeth based on the autofluorescence further comprises:
        distinguish, by the processor, the plaque area and the calculus area according to a first autofluorescence cycle of the calculus and a second autofluorescence cycle of the plaque during the time period.

2. The method for distinguishing plaque and calculus as claimed in claim 1, wherein the modulation waveform is a triangular waveform.

3. The method for distinguishing plaque and calculus as claimed in claim 1, wherein the blue light-emitting diode emits blue light within a wavelength band from 370 nanometers (nm) to 430 nm.

4. A device for distinguishing plaque and calculus, comprising:
    a blue light-emitting diode, emitting blue light to illuminate teeth in an oral cavity, wherein the blue light is used to generate autofluorescence of plaque and calculus on the teeth;
    an image sensor, sensing the autofluorescence of plaque and calculus; and
    a processor, distinguishing a plaque area and a calculus area on the teeth based on the autofluorescence;
    wherein the blue light-emitting diode emits blue light within the same wavelength band during a time period, and the blue light-emitting diode emits blue light during the time period with a light source output power having a modulation waveform;
    wherein the step of distinguishing a plaque area and a calculus area on the teeth based on the autofluorescence further comprises:
        distinguish the plaque area and the calculus area according to a first autofluorescence cycle of the calculus and a second autofluorescence cycle of the plaque during the time period.

5. The device for distinguishing plaque and calculus as claimed in claim 4, wherein the modulation waveform is a triangular waveform.

6. The device for distinguishing plaque and calculus as claimed in claim 4, wherein the blue light-emitting diode emits blue light within a wavelength band from 370 nanometers (nm) to 430 nm.

* * * * *